(12) United States Patent
Abedin et al.

(10) Patent No.: US 11,364,331 B2
(45) Date of Patent: Jun. 21, 2022

(54) METHODS AND SYSTEMS FOR MAINTAINING PATIENT FLUID BALANCE DURING AN EXTRACORPOREAL THERAPEUTIC CELL TREATMENT

(71) Applicant: Fenwal, Inc., Lake Zurich, IL (US)

(72) Inventors: Tanima Jahan Abedin, Chicago, IL (US); Katherine Radwanski, Highland Park, IL (US)

(73) Assignee: Fenwal, Inc., Lake Zurich, IL (US)

( * ) Notice: Subject to any disclaimer, the term of this patent is extended or adjusted under 35 U.S.C. 154(b) by 1172 days.

(21) Appl. No.: 15/709,773

(22) Filed: Sep. 20, 2017

(65) Prior Publication Data

US 2018/0078696 A1 Mar. 22, 2018

Related U.S. Application Data

(60) Provisional application No. 62/397,753, filed on Sep. 21, 2016.

(51) Int. Cl.
*A61M 1/36* (2006.01)
*A61M 1/38* (2006.01)
(Continued)

(52) U.S. Cl.
CPC ........... *A61M 1/3646* (2014.02); *A61K 35/14* (2013.01); *A61K 35/15* (2013.01); *A61K 35/17* (2013.01); *A61K 41/0066* (2013.01); *A61M 1/361* (2014.02); *A61M 1/3643* (2013.01); *A61M 1/3681* (2013.01); *A61M 1/3696* (2014.02); *A61M 1/38* (2013.01); *B01D 1/00* (2013.01); *B01D 21/262* (2013.01); *A61M 1/3672* (2013.01); *A61M 1/3683* (2014.02); *A61M 2202/0439* (2013.01); *A61M 2205/12* (2013.01);
(Continued)

(58) Field of Classification Search
CPC .............. A61M 1/3646; A61M 1/3643; A61M 1/3696; A61M 1/3681; A61M 1/3683; A61K 41/0066; B01D 21/262
See application file for complete search history.

(56) References Cited

U.S. PATENT DOCUMENTS

| 5,316,667 A | 5/1994 | Brown et al. |
| 6,027,657 A * | 2/2000 | Min .................... A61M 1/3693 210/782 |

(Continued)

FOREIGN PATENT DOCUMENTS

| EP | 0 952 858 A1 | 11/1999 |
| EP | 3 026 107 A1 | 6/2016 |

(Continued)

OTHER PUBLICATIONS

Europesn Search Report, dated Feb. 13, 2018 for Application No. EP 17192022.06.

*Primary Examiner* — Tatyana Zalukaeva
*Assistant Examiner* — Nhu Q. Tran
(74) *Attorney, Agent, or Firm* — Cook Alex Ltd.

(57) ABSTRACT

Methods and systems for maintaining patient fluid balance during an extracorporeal cell treatment are disclosed. The method includes minimizing the amount of saline or other fluid that is returned to the donor. Saline used during priming of the fluid circuit may be used to increase the volume of the collected cells to arrive at a treatment-ready product with a suitable hematocrit.

13 Claims, 11 Drawing Sheets

(51) Int. Cl.
  *B01D 1/00* (2006.01)
  *A61K 35/14* (2015.01)
  *A61K 35/15* (2015.01)
  *A61K 35/17* (2015.01)
  *A61K 41/00* (2020.01)
  *B01D 21/26* (2006.01)
(52) U.S. Cl.
  CPC . *A61M 2205/331* (2013.01); *A61M 2205/505* (2013.01)

(56) References Cited

U.S. PATENT DOCUMENTS

| | | | |
|---|---|---|---|
| 6,491,656 B1* | 12/2002 | Morris | A61M 1/3681 604/6.09 |
| 2006/0155236 A1* | 7/2006 | Gara | A61M 1/3633 604/4.01 |

FOREIGN PATENT DOCUMENTS

| | | |
|---|---|---|
| EP | 3 053 616 A1 | 8/2016 |
| WO | WO 98/22163 | 5/1998 |

\* cited by examiner

METHODS AND SYSTEMS FOR MAINTAINING PATIENT FLUID BALANCE DURING AN EXTRACORPOREAL THERAPEUTIC CELL TREATMENT

CROSS-REFERENCE TO RELATED APPLICATION

This application claims the benefit of and priority to U.S. Provisional Patent Application Ser. No. 62/397,753, filed on Sep. 21, 2016, the disclosure of which is incorporated herein by reference in its entirety.

FIELD OF THE DISCLOSURE

The present disclosure is directed to the processing and administration of blood products in an extracorporeal therapeutic cell treatment. More particularly, the present disclosure is directed to methods and systems for maintaining fluid balance during the processing and administering of a blood product such as a treated blood product including, but not limited to, a treated mononuclear cell product. Even more particularly, the present disclosure is directed to methods and systems that limit the introduction of excess fluid into the extracorporeal circuit which would otherwise be infused to the patient during an extracorporeal cell treatment and affect patient fluid balance.

BACKGROUND

Whole blood can be separated into its constituent components (cellular or liquid), and the desired component can be separated so that it can be administered to a patient in need of that particular component. For example, mononuclear cells (MNCs), primarily lymphocytes and monocytes, can be removed from the whole blood of a patient, collected, and subjected to photodynamic therapy in a procedure commonly referred to as extracorporeal photopheresis, or ECP. In ECP, MNCs are treated with a photosensitizing agent (e.g., 8-methoxypsoralen (8-MOP)), subsequently irradiated with specified wavelengths of light to achieve a desired effect, and returned to the patient for the treatment of various blood diseases to, e.g., eliminate immunogenicity in cells, inactivate or kill selected cells, inactivate viruses or bacteria, or activate desirable immune responses.

In one example of an ECP procedure, blood is withdrawn from the patient and the mononuclear cells are separated (typically by centrifugation) from the remainder of the whole blood components. The separated mononuclear cells are combined with a selected dose of 8-MOP and subjected to light (typically UV-A) to activate the 8-MOP molecules. The light crosslinks 8-MOP to DNA strands inside the cell and on the cell wall of the exposed mononuclear cells, eventually causing cell apoptosis. The fluid with the altered mononuclear cells is reinfused back into the patient to induce an immune system response. Examples of a photopheresis methods and systems of the type described above are set forth in U.S. Pat. No. 9,399,093 and U.S. Patent Application Publication No. US2014/0370491, the contents of both incorporated herein by reference in their entireties.

In order to administer an effective amount of activating light (e.g., UV-A) to the mononuclear cells, the mononuclear cell product must have a hematocrit and thickness that allows for the administered light to be effective in the treatment of the mononuclear cells. For example, if the hematocrit is too high—indicating too many red cells—the residual red blood cells may interfere with the light treatment, i.e., activation of the photoactivation agent, resulting in a less than fully treated mononuclear cell product. A conditioning solution, such as saline, may be used to increase the volume of and dilute the fluid in which the collected mononuclear cells reside to ensure that the correct thickness and hematocrit is reached in the container of cells to be treated, thereby arriving at a "treatment-ready" product. The photoactivation agent is likewise added to the mononuclear cells (e.g., in an irradiation container) and this mixture is irradiated in an illumination device with light. The treated cells are then returned to the patient.

One of the potential drawbacks of adding additional fluid to the collected and to-be-treated mononuclear cells is that it may result in excess fluid volume being infused to the donor. For example, saline is commonly used in other phases of an ECP procedure such as during priming of the disposable fluid circuit and rinsing out the disposable fluid circuit (i.e., the "kit") contents during reinfusion. The saline (or other added solution) used in the priming and reinfusion sequences is typically infused into the patient with the treated product. Thus, the combined volume of the saline used to prime the disposable fluid circuit, rinsing out the kit contents, and the saline used to increase the volume of the cell product (re)infused to the patient may result in a patient fluid balance that can be undesirably positive. Accordingly, it would be desirable to provide a method and system that maintains the fluid balance of the patient within acceptable levels and/or avoids or at least limits the addition of excess fluid during the procedure which would otherwise be returned or infused to the patient.

SUMMARY

There are several aspects to the subject matter disclosed herein. In one aspect, the subject matter of this disclosure is directed to a method for maintaining fluid balance in a patient undergoing a therapeutic cellular treatment. The method includes priming a fluid flow path of a disposable fluid circuit mounted on a reusable hardware unit with a predetermined volume of a priming solution, and diverting at least a portion of the pre-determined volume of the priming solution from the flow path of the fluid circuit. The method further includes collecting a target cell population from a patient in fluid communication with the fluid circuit and combining the diverted priming solution with the target cell population to arrive at a treatment-ready product. The treatment-ready product is then treated and the now-treated product is administered to the patient.

In another aspect, the subject matter disclosed herein is directed to a method for maintaining fluid balance in a patient undergoing a therapeutic cellular treatment that includes priming a fluid flow path of a disposable fluid circuit mounted on a reusable hardware unit with a predetermined volume of a priming fluid, collecting a target cell population from a patient in fluid communication with the fluid circuit and combining a solution different from the priming fluid with the target cell population to arrive at a treatment-ready product. The method further includes treating the treatment-ready product to arrive at a treated cellular product, administering the priming solution to said patient, and administering the treated cellular product to the patient.

In yet another aspect, the subject matter disclosed herein is directed to a system for performing a therapeutic cellular treatment. The system includes a separation unit for effecting separation of whole blood into two or more components, a treatment unit for treating a target cell population and a disposable fluid circuit having a patient access device, tubing defining a flow path between the patient access device, a separation chamber, a treatment chamber and one or more containers for collecting a separated component. The system includes one or more pumps and one or more valves adapted to interact with the flow paths of the fluid circuit and effect flow of fluid through the flow paths. A detector configured to monitor the separation of whole blood into the two or more components is included as is a controller. The controller is configured to receive signals from the detector, effect operation of the one more pumps to divert at least a portion of a priming solution from the flow path of the circuit to the one or more containers for collecting a separated component.

DETAILED DESCRIPTION OF THE EMBODIMENTS

The present disclosure is directed to methods and systems for the collection, treatment and reinfusion of mononuclear cells. The methods and systems of the present disclosure are described in connection with particular apheresis and irradiation/illumination devices for purposes of exemplification only. It will be understood that the methods and systems described and claimed herein may be carried out and provided in combination with other apheresis and/or irradiation/illumination devices that will be known to those of skill in the art.

Figure 1:
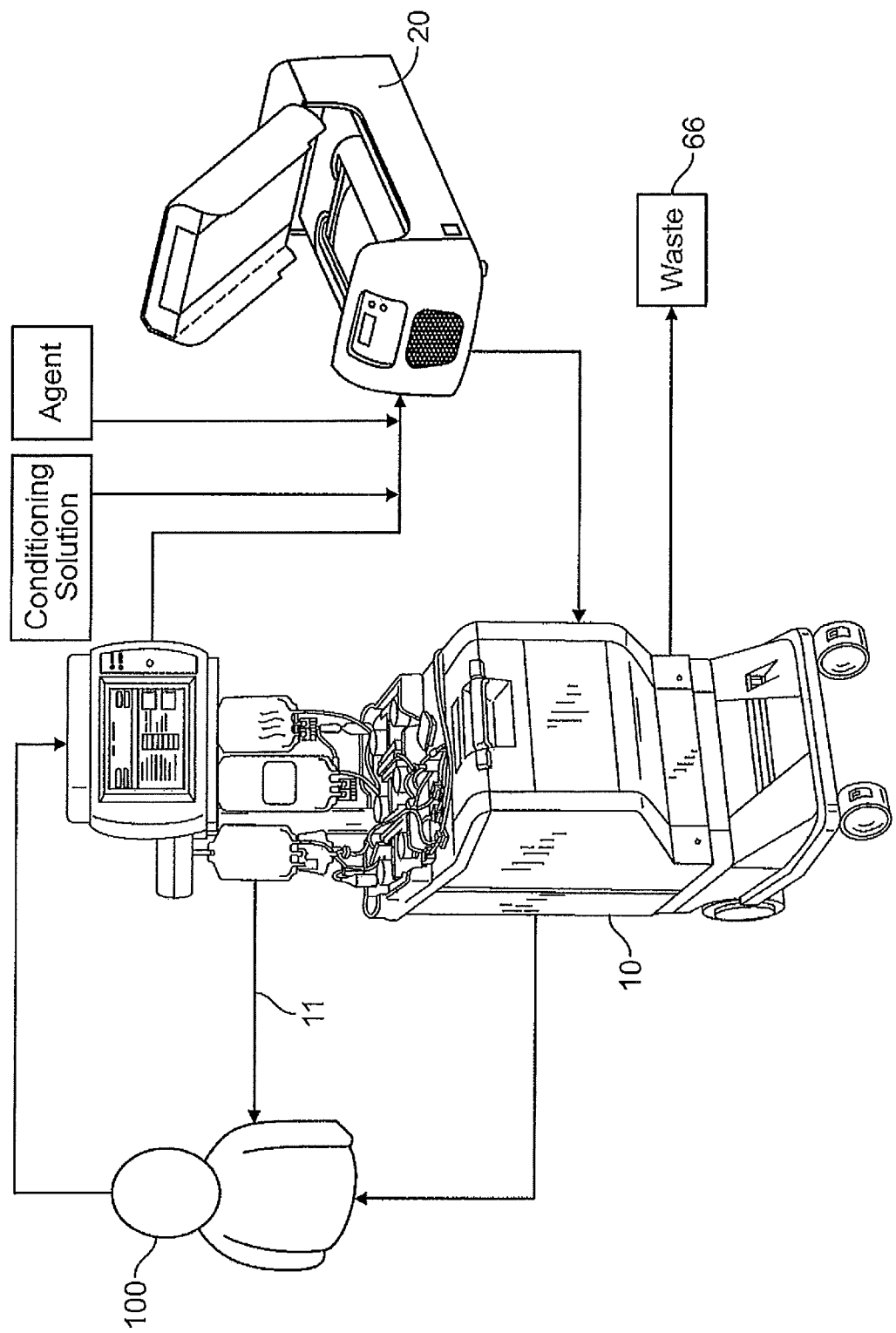
FIG. 1 is a diagram of the system and method for processing a mononuclear cell product in accordance with the present disclosure.

Turning now to the Figures, FIG. 1 diagrammatically shows the system and processing steps in the method described herein. In accordance with the present disclosure, the system includes a separation unit or separator 10 and a treatment or irradiation unit 20. In one embodiment, irradiation unit 20 is independent and housed separately from separator 10. Although separately housed and independent devices, it is preferable that separator 10 and irradiation device 20 be located adjacent to each other. While FIG. 1 shows a preferred embodiment of the individual separation and irradiation units, it will be appreciated that the methods described herein may also be used with devices having integrated separation and irradiation components housed in one device.

As generally shown in FIG. 1, whole blood is withdrawn from the patient 100 and introduced into the separator 10 where the whole blood is separated to provide a target cell population. More particularly, whole blood is withdrawn from the patient through venipuncture needle 82 (FIG. 2) and introduced into the separation chamber of separation container 14 (FIGS. 2 and 4) carried within and/or mounted on a centrifuge device of separator 10. Within the separator 10, the target cell population is separated from other components. In a preferred embodiment in accordance with the present disclosure, the target cell population is the patient's mononuclear cells (MNC). Other components separated from the whole blood in this initial separation, such as red blood cells, plasma and platelets, may be returned to the patient or collected in pre-attached containers of the blood processing set or kit, as shown by line 11. The collection of mononuclear cells is more specifically described in U.S. Pat. No. 6,027,657, the contents of which are incorporated herein by reference.

The separated target cell population, e.g., mononuclear cells with residual red blood cells and plasma, is then prepared for treatment and irradiation in treatment component 20. In accordance with the present disclosure, effective treatment of the mononuclear cells with ultraviolet light requires that the collected mononuclear cells be provided in a suspension having a suitable hematocrit, i.e., a certain (low) concentration of red blood cells. Specifically, the hematocrit level in the MNC suspension to be treated affects the amount of UV light that the MNC are exposed to as the red blood cells in the MNC suspension will block at least a portion the UV light from reaching the targeted MNCs. In accordance with the methods and systems described herein, a suitable hematocrit may be 1 to 5%.

In order to prepare or otherwise condition the collected mononuclear cells for the photoactivation treatment, the collected cell product may be combined (diluted) with a conditioning solution to adjust the hematocrit of the collected cell product and arrive at a selected thickness of the cell product in the treatment container to allow for effective and at least substantially complete treatment of the product within the treatment chamber of treatment apparatus 20. The collected cell product is also combined with an effective amount of the photoactivation agent. As shown in FIG. 1, addition of the conditioning solution and the photoactivation agent may occur after collection of the desired cellular product in separator 10. As described below, the conditioning solution may be added from a container 64 (shown in FIG. 2) directly to the container that holds the collected MNCs. The photoactivation agent may likewise be added from a container or by a syringe or other delivery device. Alternatively, the conditioning solution and/or photoactivation agent may be introduced elsewhere in the processing circuit 200 of FIG. 2 for combination with the collected cell product (in, for example, container 68). In one embodiment, the conditioning solution may be saline and the photoactive agent may be 8-methoxypsoralen (8-MOP).

Turning now, more specifically, to one embodiment of the reusable hardware and disposable fluid circuit components of the system, device/separator 10 useful in the collection (and washing) of mononuclear cells include the Amicus® Separator made and sold by Fresenius-Kabi USA, of Lake Zurich, Ill. Mononuclear cell collections using a device such as the Amicus® are described in greater detail in U.S. Pat. No. 6,027,657, previously incorporated by reference herein in its entirety.

Figure 2:
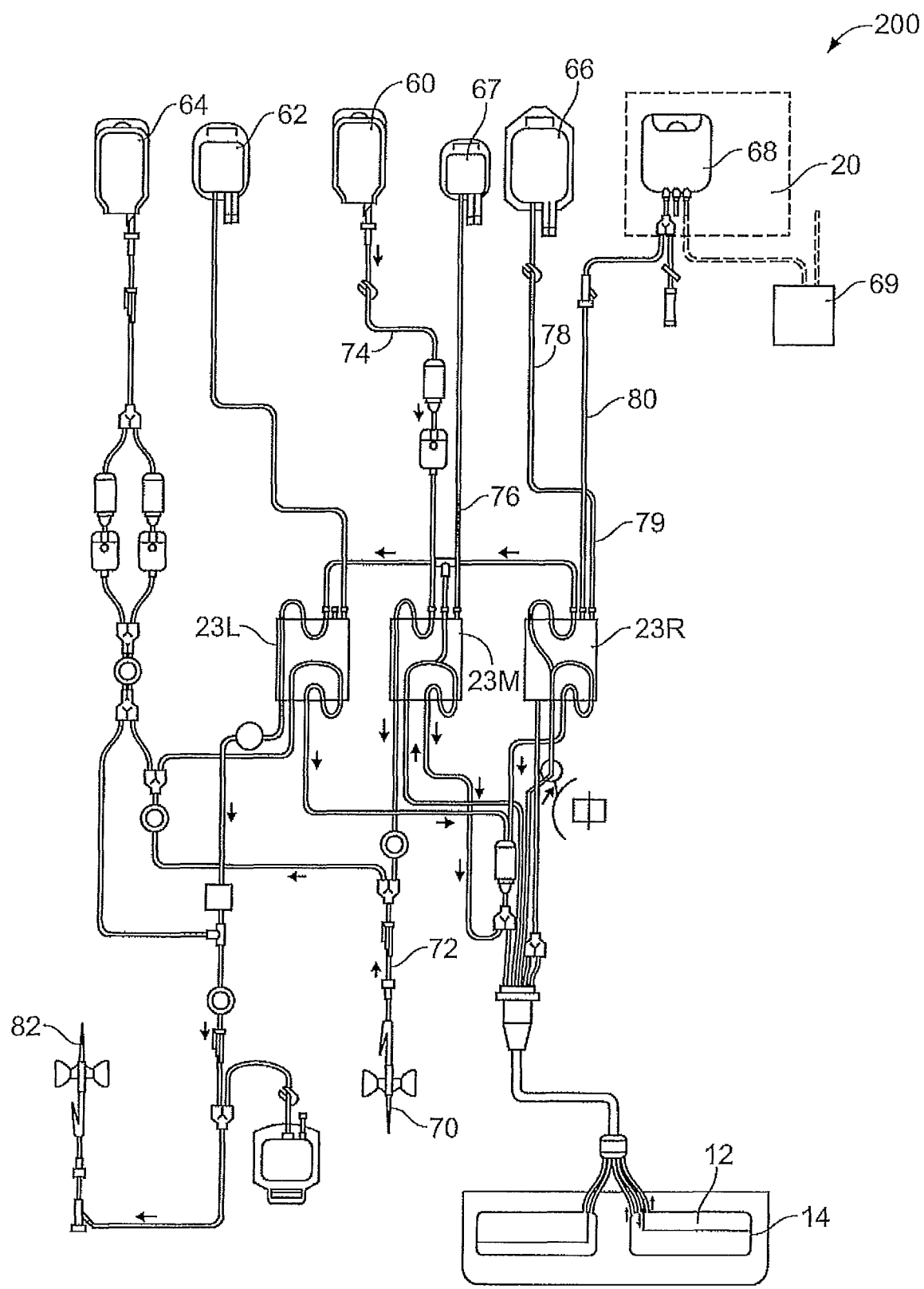
FIG. 2 is a diagram of a disposable fluid circuit suitable for use with the system described herein.
Figure 3:
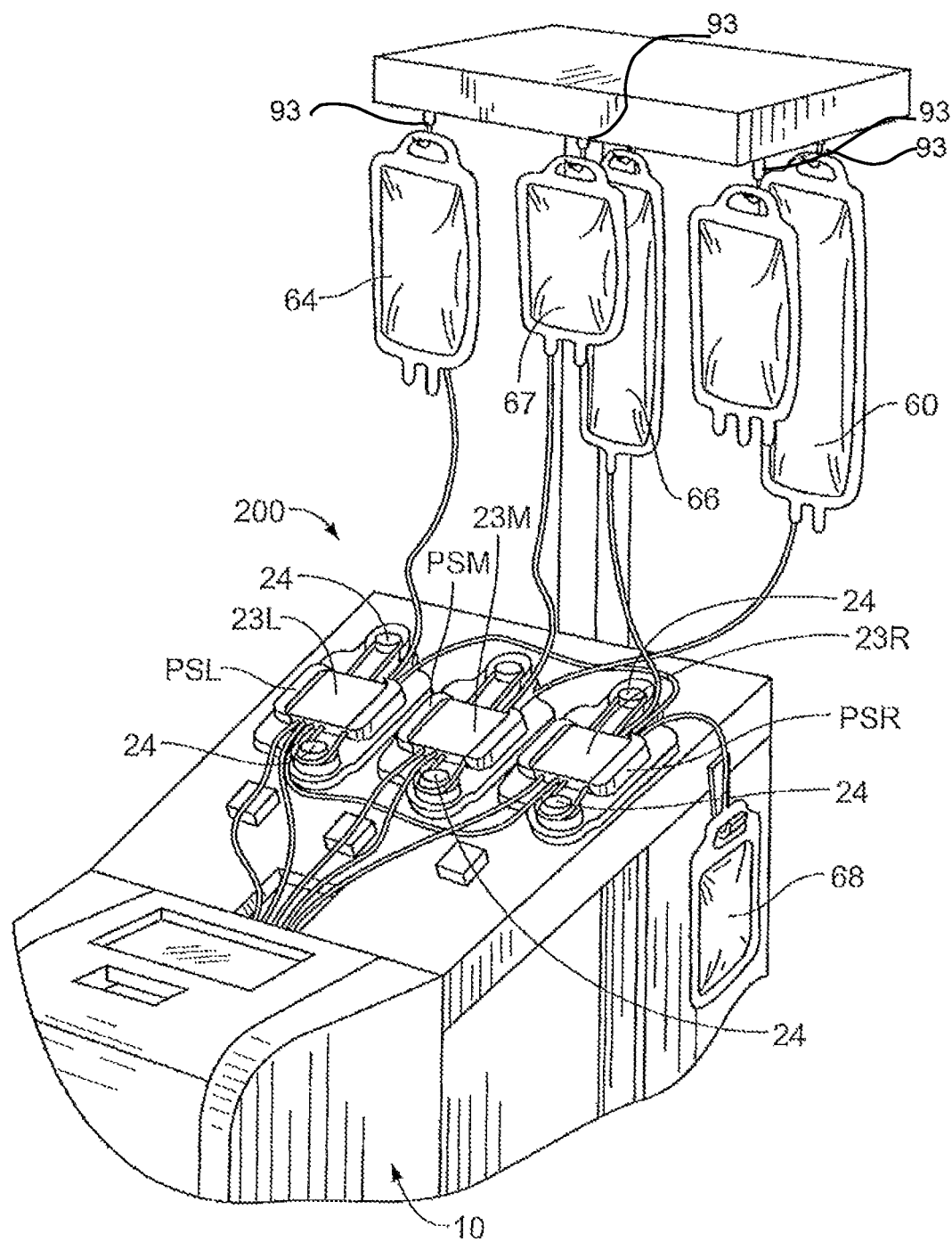
FIG. 3 is a partial perspective view of the front panel of a multifunctional apheresis separator useful in the methods and systems described herein with the disposable fluid circuit mounted thereon.
Figure 4:
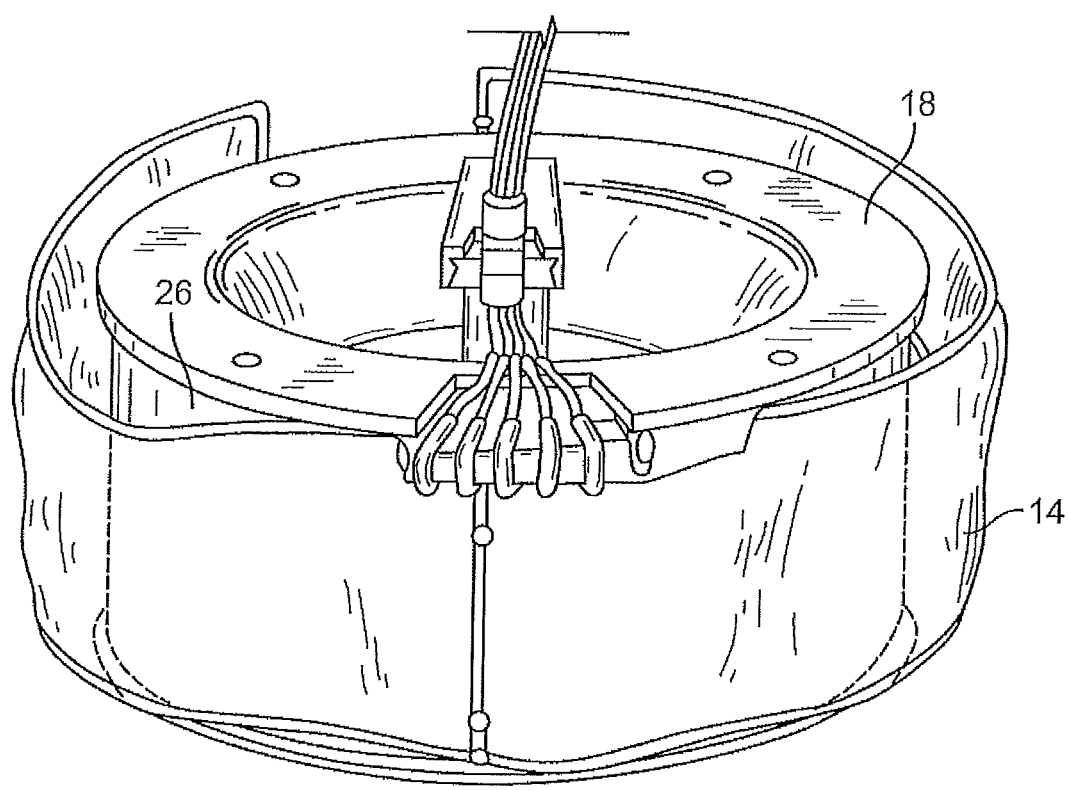
FIG. 4 is a perspective view of a processing container (separation chamber) of the fluid circuit used with the separator.

Briefly, FIGS. 3-4 show a representative blood centrifuge device/separator 10 with fluid circuit 200 mounted thereon, the fluid circuit 200 having a blood processing container 14 (see FIG. 2) defining a separation chamber suitable for harvesting mononuclear cells from whole blood. As shown in FIG. 3, a portion of disposable processing set or fluid circuit 200 is mounted on the front panel of device/separator 10. As also shown in FIG. 4, separation chamber 12, which is integral with the rest of circuit 200, is defined by the walls of a flexible processing container 14 carried within an annular gap defined by a rotating spool element 18 and an outer bowl element (not shown) housed within the cabinet of device/separator 10. The processing container 14 takes the form of an elongated tube or belt which is wrapped about the spool element 18 before use. The bowl and spool element 18 are pivoted on a yoke between an upright position and a suspended position, also not shown. In operation, the centrifuge device within separator 10 rotates the suspended bowl and spool element 18 about an axis, creating a centrifugal field within the processing chamber 12 of container 14. Details of the mechanism for causing relative movement of the spool 18 and bowl elements as just described are disclosed in U.S. Pat. No. 5,360,542 entitled "Centrifuge with Separable Bowl and Spool Elements Providing Access to the Separation Chamber," which is also incorporated herein by reference.

Figure 7:
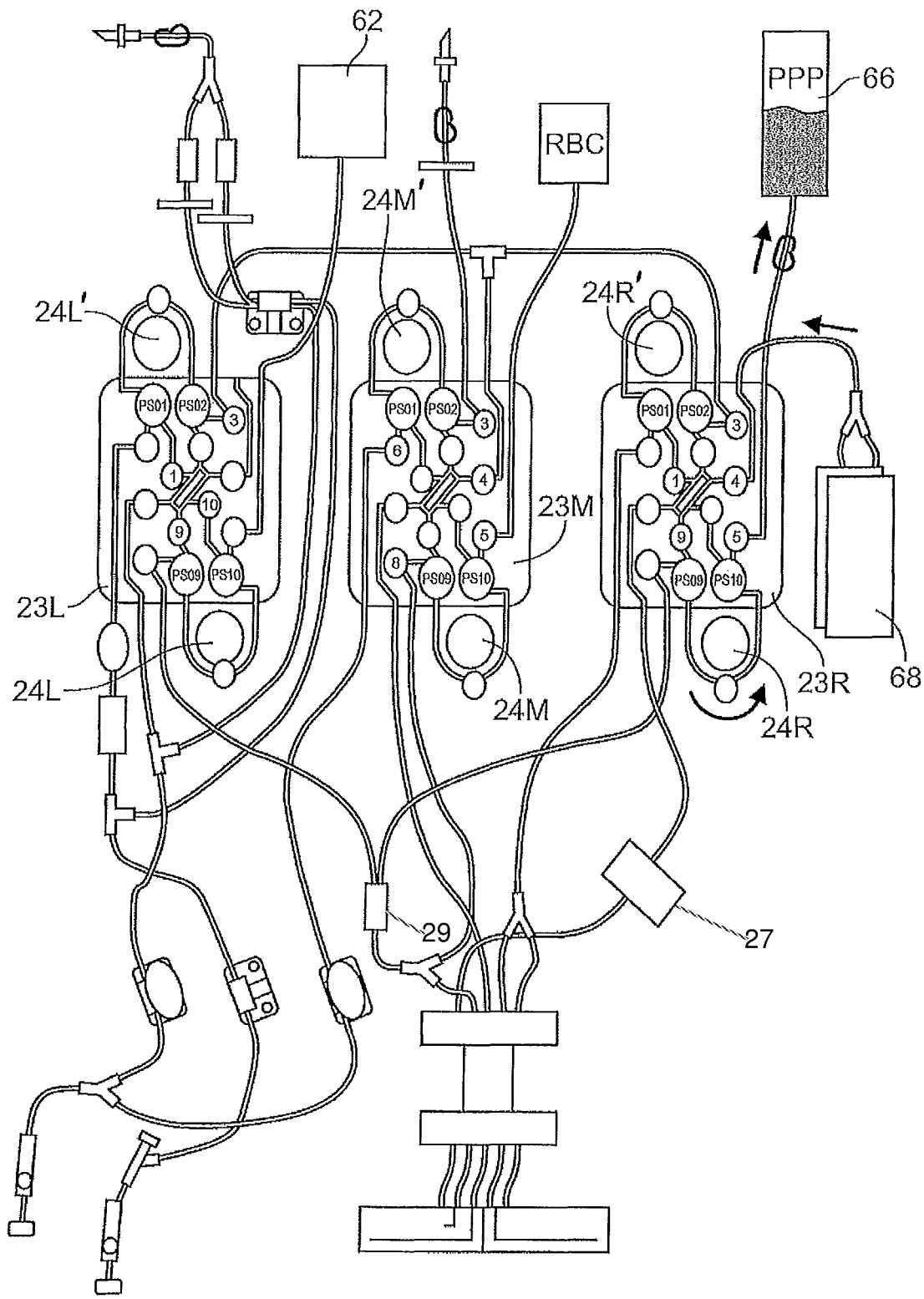
FIG. 7 is a diagram of the disposable fluid processing circuit and the flow of fluid through said circuit during one phase of the method of the present disclosure.

With reference to FIGS. 2-3, fluid circuit 200 includes a plurality of processing fluid flow cassettes 23L, 23M and 23R with tubing loops for association with peristaltic pumps 24 on device 10. As described in U.S. Pat. No. 6,027,657, previously incorporated by reference, cassettes 23L, 23M and 23R include molded plastic bodies with integrally molded liquid flow channels. Valve stations (depicted as numbered circles within each cassette and best seen in FIG. 7) are molded into the backside of cassette bodies. A flexible diaphragm covers and seals the backside of the cassette (23) body. Valve stations align with valve actuators of pump stations (PSL, PSM and PSR) located on the front panel of device 10. Fluid circuit 200 also includes a network of tubing and pre-connected containers for establishing flow communication with the patient and for processing and collecting fluids and blood and blood components, as shown in greater detail in FIG. 2.

In one embodiment, as seen in FIGS. 2 and 3, disposable processing set 200 may include a container 60 for supplying anticoagulant, a waste container 62 for collecting waste from one or more steps in the process for collecting, treating and/or washing mononuclear cells, a container 64 for holding saline or other priming or conditioning medium, a container 66 for collecting plasma, a container 68 for collecting the mononuclear cells and, optionally, container 69 for holding the photoactivation agent.

Container 68 may also serve as the illumination container, and is preferably pre-attached to the disposable set 200. Alternatively, container 68 may be attached to set 200 by known sterile connection techniques, such as sterile docking or the like. With reference to FIG. 2, fluid circuit includes inlet line 72, an anticoagulant (AC) line 74 for delivering AC from container 60, an RBC line 76 for conveying red blood cells from chamber 12 of container 14 to container 67, a platelet-poor plasma (PPP) line 78 for conveying PPP to container 66 and line 80 for conveying mononuclear cells to and from separation chamber 14 and collection/illumination container 68. The blood processing set includes one or more patient access device(s) such as venipuncture needle(s) for accessing the circulatory system of the patient. As shown in FIG. 2, fluid circuit 200 includes inlet needle 82 and return needle 70. In an alternative embodiment, a single needle can serve as both the inlet and outlet needle.

Container 68 is suitable for irradiation by light of a selected wavelength. By "suitable for irradiation" it is meant that the walls of the container are sufficiently transparent to light of the selected wavelength to activate the photoactive agent. In treatments using UVA light, for example, container walls made of ethylene vinyl acetate (EVA) are suitable. Accordingly, as indicated above, container 68 in which the mononuclear cells are collected may serve both as the collection container and the irradiation container. Container 68 may be placed inside irradiation device 20 by the operator or, more preferably, may be placed inside the irradiation chamber of irradiation device 20 at the beginning of the ECP procedure and prior to whole blood withdrawal (as shown by the broken lines representing device 20 in FIG. 2). In any event, container 68 preferably remains integrally connected to the remainder of fluid circuit 200 during the entire procedure, thereby maintaining the closed or functionally closed condition of fluid circuit 200.

Fluid flow through fluid circuit 200 is preferably driven, controlled and adjusted by a microprocessor-based controller in cooperation with the valves, pumps, weight scales and sensors of device 10, the details of which are described in the previously mentioned U.S. Pat. No. 6,027,657. As described below, the controller is programmed to activate rotation of pumps (and control the rotational speed thereof), associated with cassettes 23L, 23M and 23R, open and close valves, receive output signals from sensors and detectors, such as the interface detection system described below, and, preferably, to commence and control treatment of the MNC in the treatment unit (i.e., irradiation device) 20.

Figure 5:
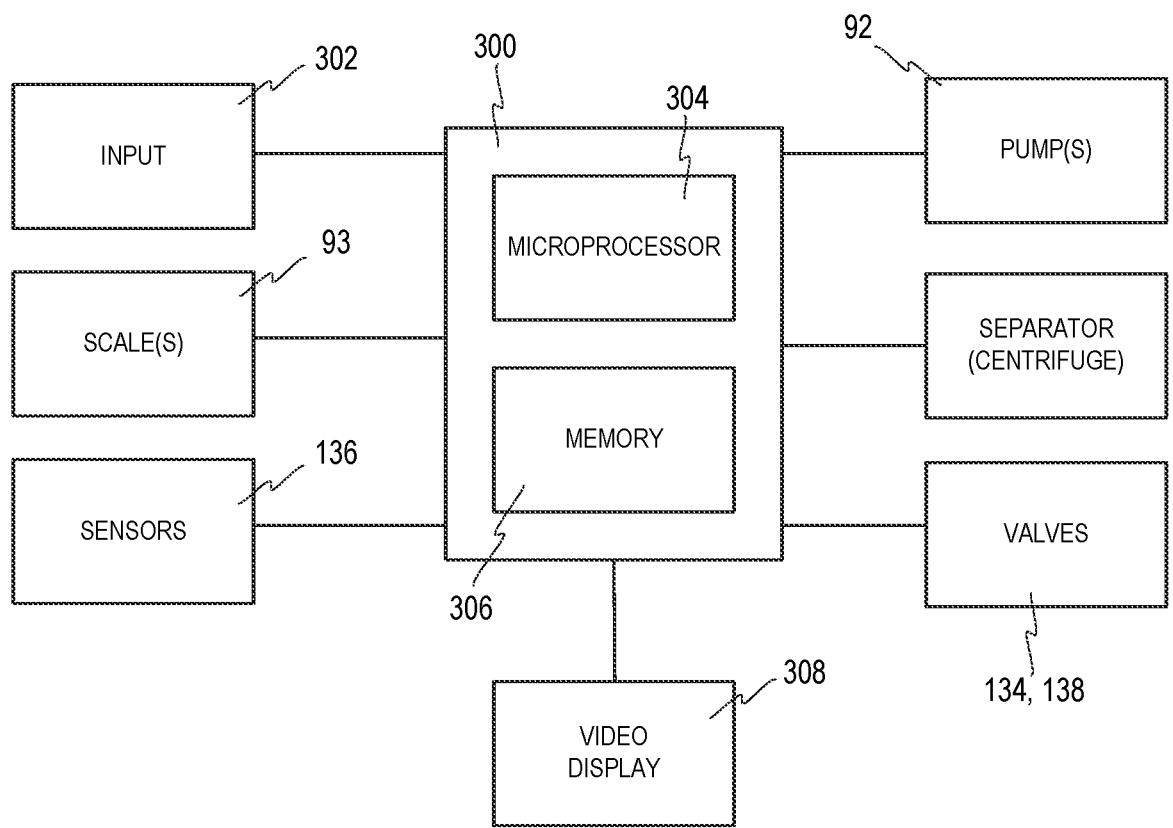
FIG. 5 is a schematic view of the control circuitry, including the controller, of the system of FIG. 1.

FIG. 5 is a schematic view of the control unit or "controller" 300 included in device 10 of the present disclosure. Controller 300 may include a microprocessor 304 (which may include multiple physical and/or virtual processors). According to other embodiments, the controller 300 may include one or more electrical circuits designed to carry out the actions described herein. In an embodiment, controller 300 may include a microprocessor and other circuits or circuitry. In addition, controller 300 may include one or more memories 306. The instructions by which microprocessor 304 is programmed may be stored on the memory 306 associated with microprocessor 304, which memory/memories 306 may include one or more tangible non-transitory computer readable memories, having computer executable instructions stored thereon, which when executed by microprocessor 304, may cause the microprocessors 304 to carry out one or more actions as described herein.

As is also illustrated in FIG. 5, controller 300 may be coupled to one or more of the structures described herein, for example to receive information (e.g., in the form of signals) from these structures or to provide commands (e.g., in the form of signals) to these structures to control the operation of the structures. As illustrated in FIG. 5, controller 300 may be coupled to weight scales 93 (also seen in FIG. 3) that hold solution containers or that are provided to collect separated blood components, the sensors associated with device 10, or more specifically with the cassettes 24L, 24M, and 24R, the valve assemblies 132 and the at least one input 302 to receive information from those devices. Additionally, controller 300 may be coupled to pumps 24 and the separator (centrifuge) drive unit (not shown) to provide commands to those devices and to control their operation. It may also be possible that controller 300 receives information from and provides commands to a given structure, such as one of the structures already mentioned. Controller 300 may be directly electrically connected to these structures to be coupled to them, or controller 300 may be directly connected to other intermediate equipment that is directly connected to these structures to be coupled to them.

The at least one input 302 may include a number of different devices according to the embodiments described herein. For example, input 302 could include a keyboard or keypad by which a user may provide information and/or instructions to controller 300. Alternatively, input 302 may be a touch screen, such as may be used in conjunction with a video display 308 (FIG. 1) that is disposed on the front panel of the device 10, video display 308 also being coupled to the controller 300. The assembly of the input/touch screen 302 and video display 308 may be one of the aforementioned structures to which controller 300 is coupled from which controller 300 receives information and to which controller 300 provides commands.

The system may include an interface detecting unit that monitors the location of the interface between separated fractions of the fluids being processed. The interface detection unit may be of the type described in U.S. Pat. No. 6,027,657, previously incorporated by reference. The interface detection unit may be the same interface detection unit used during the initial separation of whole blood into two or more components. After the initial separation has been completed and separation chamber 12 is used to separate the treated mononuclear cell fraction from the supernatant fraction, and, as described below, saline from blood component fractions. The interface detection unit monitors the location of the interfaces between these fractions.

Figure 6A:
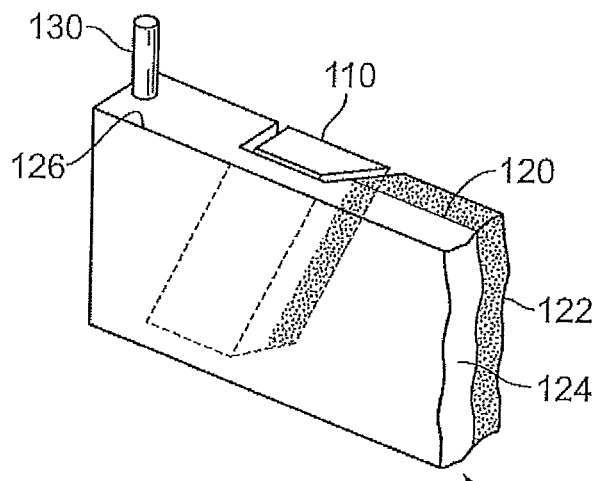
FIG. 6(a)-6(c) is a series of enlarged perspective views of an interface ramp carried by the centrifuge and the interface between the treated mononuclear cell fraction and an adjacent fraction in different locations (a)-(c)
Figure 6B:
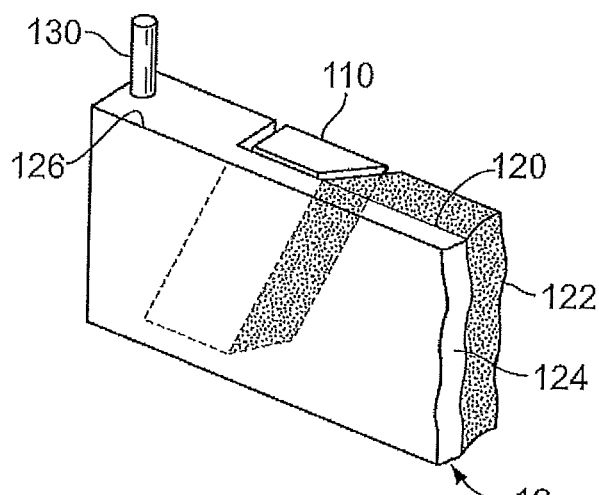
Figure 6C:
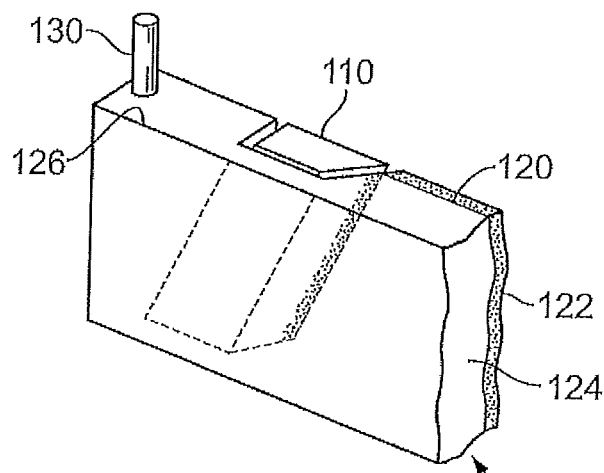

As described in U.S. Pat. No. 6,027,657, a ramp 110 may be provided in combination with a light source and a light detector to determine the radial position of the interface between red blood cells and plasma during initial whole blood separation and, as described below, between saline and plasma or other blood components. FIGS. 6(a)-6(c) show an exemplary ramp 110 which extends from the inner surface of the bowl (not shown) toward spool 18 (FIG. 4).

As shown in FIGS. 6(a)-6(c), during the step of separating one fraction from another fraction, an interface 120 is formed between the fractions in separation chamber 12. The heavier fraction 122 accumulates along the "high G" wall, while a lighter fraction 124 occupies the area of chamber 12 nearer the "low G" wall 126. An exit port 130 communicates with chamber 12 and allows for removal of the lighter (e.g., supernatant) fraction from chamber 12 and diversion of such fraction 124 to an appropriate container. In accordance with the present disclosure, interface 120 is optimally positioned such that substantially all of the lighter fraction can exit chamber 12 through port 130 to the substantial exclusion of the heavier fraction 122. If interface 120 is positioned too close to the "high G" wall, as shown in FIG. 6(c), some of the lighter fraction (e.g., excess conditioning fluid) will undesirably be sent back to the patient. On the other hand, if interface 120 approaches the "low G" wall 126, as shown in FIG. 6(b), some of the heavier fraction treated mononuclear cell fraction 124 will undesirably be diverted to waste container 66.

Thus, if the interface detector unit senses the position of interface 120 outside of its optimal position, as shown in FIG. 6(a), for example, it will send a signal output to the controller, as also described in U.S. Pat. No. 5,316,667, incorporated herein by reference. The controller, in turn, will adjust the speed of the peristaltic pump associated with cassette that acts on the line leading to the appropriate container to accelerate or slow the rotation of such pump and thereby adjust the interface to its more optimal position. In one embodiment, the speed of pump rotation of the pump responsible for introducing fluid into separation chamber 12 (for example, pump 24L) associated with cassette 23L may be fixed. The speed of pump 24R which may be associated with the flow path for removing the lighter fraction from separation chamber 12 may be varied by the controller depending on the location of the interface between the treated mononuclear cell fraction and the adjacent fraction.

Thus, for example, in connection with the processing of mononuclear cells in accordance with the methods and systems described herein, whole blood is withdrawn from a patient 100 through inlet needle 70 and is introduced into separation chamber 12 of container 14. As described in U.S. Pat. No. 6,027,657, previously incorporated by reference, whole blood is separated into its components. A pre-determined amount of PPP may be diverted to plasma container 66 where it can be later added (in combination with diverted saline) to the collected mononuclear cells and thereby arrive at the desired mononuclear cell product hematocrit. Whole blood continues to be separated into RBCs, MNCs, platelet-rich plasma (PRP) and PPP. RBCs and PRP are returned to the donor, while the desired mononuclear cells accumulate in the separation chamber. An interface 120 is established between the PPP and the fraction containing the mononuclear cells. PPP is withdrawn through the outlet port in separation chamber 12.

Once an amount of whole blood, sufficient to obtain the desired level of mononuclear cells, has been processed, some of the separated red blood cells are collected (in container 67) and used to push out the mononuclear cells that have accumulated in separation chamber 12. While the RBCs push out the mononuclear cells, PRP that has remained with the desired mononuclear cells is diverted from the separation chamber 12 and, as mentioned above, is returned to the patient. After a selected period of time, through valving under the action of controller 300, the desired mononuclear cells are diverted to illumination container 68. After another selected period of time, under the action of the controller 300, flow is again diverted to return the RBCs (that were used to push out the mononuclear cells) to the patient. This cycle is repeated until a desired volume of mononuclear cells has been collected.

Once the system, under the action of the controller 300, has combined saline/PPP with the collected mononuclear cells and the photoactivation agent added from container 69, the "treatment ready" product in container 68 is subjected to the appropriate dose of radiation. As shown in FIG. 1, once the treatment is complete, the now treated mononuclear cell product is returned to patient 100.

Figure 8:
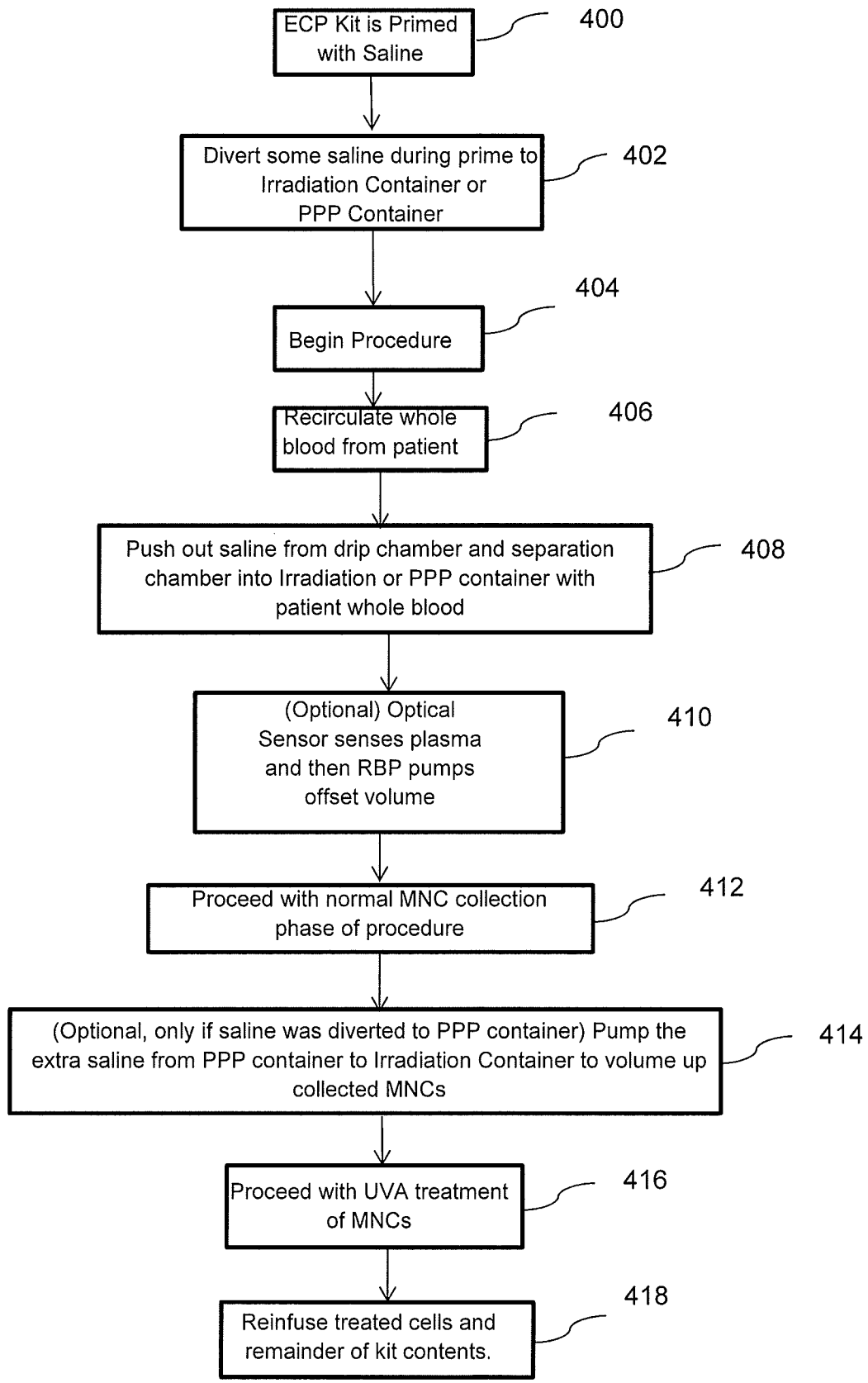
FIG. 8 is a flow chart indicating the steps of one embodiment of the method of the present disclosure.

In accordance with the present method and system described herein, the main cycle of collection and treatment is preceded by priming of the disposable fluid circuit 200. Priming, as mentioned above, clears air from the flow paths of the disposable processing circuit 200. A commonly used priming solution is saline, which may be supplied to the system from a container, such as container 64. Container 64 may be attached to fluid circuit 200 in a sterile fashion. As described in U.S. Pat. No. 6,027,657, to commence priming, controller 300 commands pumps 24 on reusable hardware unit 10 to convey the sterile priming fluid, i.e., saline, at least substantially throughout the entire fluid circuit 200, as shown in step 400 of FIG. 8, in particular. In accordance with the methods and system described herein, and with continued reference to FIG. 8, at least a portion of the saline may be diverted to container 66 (which also receives some of the PPP during initial processing). Alternatively, controller 300 may direct the pumps to divert some of the saline used for priming directly to irradiation container 68 (Step 402). Once circuit 200 has been primed, the collection and treatment of the mononuclear cells is commenced (Step 404). In one embodiment, whole blood from the patient is introduced into the circuit 200 (Step 406) and pushes saline residing in the air trap 29 and in the flow path of circuit 200 into either PPP container 66 or directly to irradiation container 68. More specifically, as whole blood from the patient fills the centrifuge, pump 24 associated with cassette 24R will pump at a rate sufficient to maintain an interface 120 (e.g., FIGS. 6(*a*)-(*c*)) between the lighter saline and the heavier fraction containing red blood cells, plasma, and platelets. Maintaining this interface allows only saline to be pumped out of separation chamber 14 (exiting through outlet 130, as described in connection with FIGS. 6A-6C) where it can be conveyed to either plasma container 66 or directly to irradiation container 68. Lower right pump 24 associated with cassette 24R will continue to pump saline until the optical detector detects that plasma is beginning to exit separation chamber 14. Once the presence of plasma has been detected by optical detector, lower right pump 24, associated with cassette 23R, will continue to pump for a period of time that corresponds to the volume of the tubing from the optical sensor 27 shown in FIG. 7 up to the PPP bag 66 or irradiation container 68 (step 410). Once this predetermined volume (i.e., "offset volume") of fluid in that portion of disposable processing set 200 has been reached, the system, under the action of the controller, will then commence with mononuclear cell collection (step 412), including further separation of red blood cells from platelet-rich plasma and the collection of the mononuclear cells in separation chamber 12 of container 14. Remaining saline in the system will be infused to the patient along with separated red blood cells.

Once a sufficient amount of MNCs have been collected in the irradiation container, pump 24 will pump the extra saline from container 66 to irradiation container 68 to dilute the collected mononuclear cells to an appropriate hematocrit (step 414). The system will then proceed with the irradiation treatment of the mononuclear cells (Step 416). Once treatment is complete, the now treated mononuclear cells are reinfused together with the remainder of any fluid in the flow path of circuit 200 to the patient (Step 418). It will be understood, that if the saline was directly conveyed to the irradiation container, the step 414 of pumping saline from PPP container 66 to irradiation container 68 may be omitted.

Thus, in accordance with the methods and systems described herein, saline from the priming sequence can be utilized to add volume to the collected mononuclear cells. This avoids the need to add additional saline from saline container 64, which would otherwise add to the total amount of saline that is returned or infused to donor 100. Accordingly, fluid balance of the patient is more easily maintained and the addition of an excessive positive fluid volume returned to the donor may be avoided.

Figure 9:
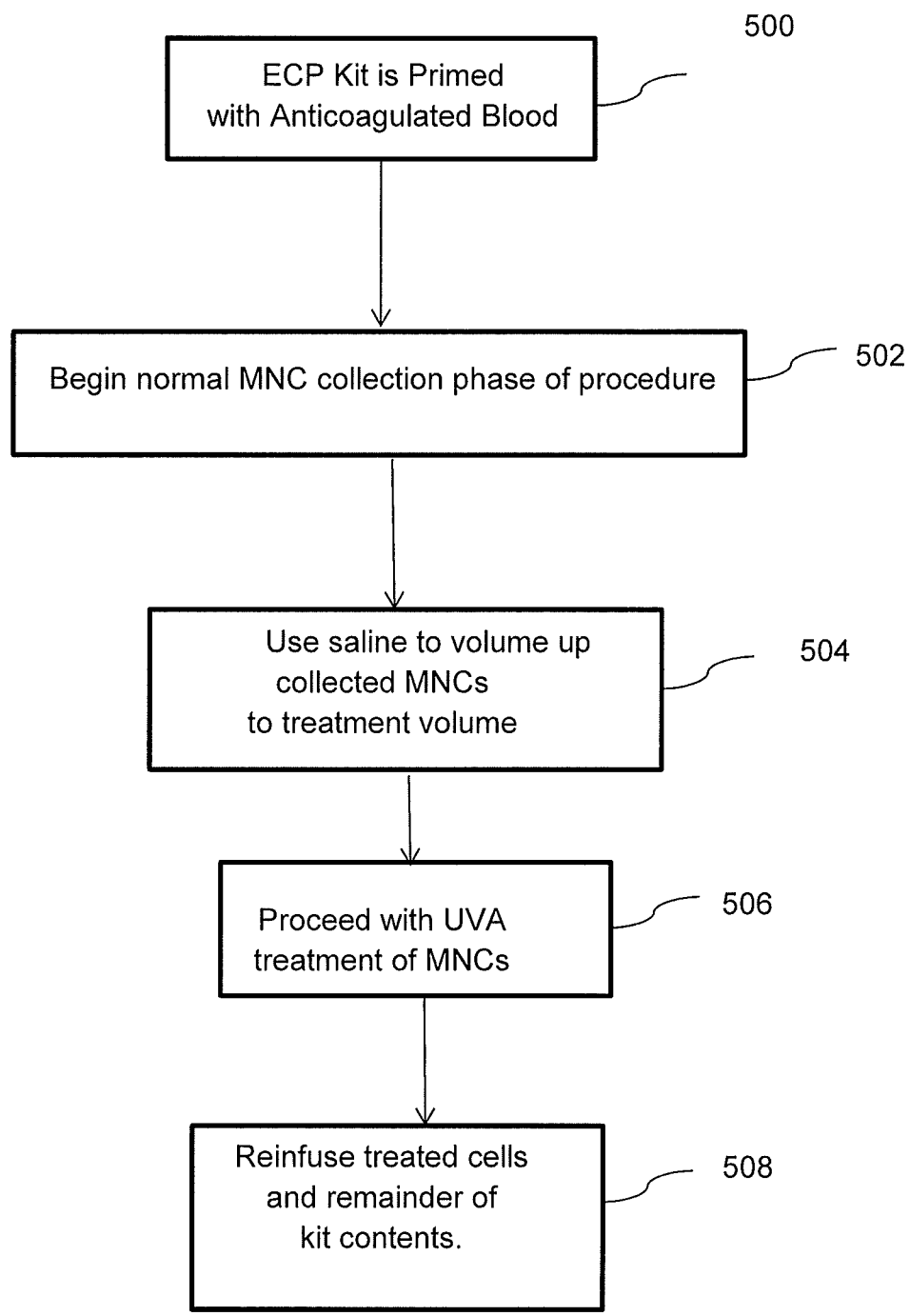
FIG. 9 is a flow chart indicating the steps of another embodiment of the method of the present disclosure.

There are other ways to reduce the amount of saline that is infused to the patient, in accordance with the present disclosure. For example, as shown in FIG. 9, the fluid circuit 200 may be primed with anticoagulated whole blood instead of saline (Step 500). Once the system has been primed with anticoagulated whole blood, controller 300 will initiate the mononuclear cell collection phase of the treatment procedure (Step 502). Saline, from saline source container 64, may be used to add additional volume to the mononuclear cells which have been collected in irradiation container 68 (and, optionally, to rinse fluid circuit). Once the desired amount of saline has been combined with the mononuclear cells, the treatment ready mononuclear cell product may be subjected to the irradiation treatment in irradiation device 20 (step 506). As described above, after treatment (Step 506) the treated cells may be recirculated through at least a portion of circuit 200 and reinfused to the patient 100 with the remainder of the kit contents By this alternative method, the combined amount of saline that would otherwise have been used for priming and for adjusting the volume of the mononuclear cell product is avoided. By priming the system with the patient's own blood (and some limited amount of anticoagulant) the added volume of fluid to the extracorporeal fluid circuit is maintained. In accordance with this alternative embodiment, approximately 120 ml less saline would be infused to the patient as compared with using saline to prime the circuit and separately add saline to adjust the volume of the mononuclear cell product.

Figure 10:
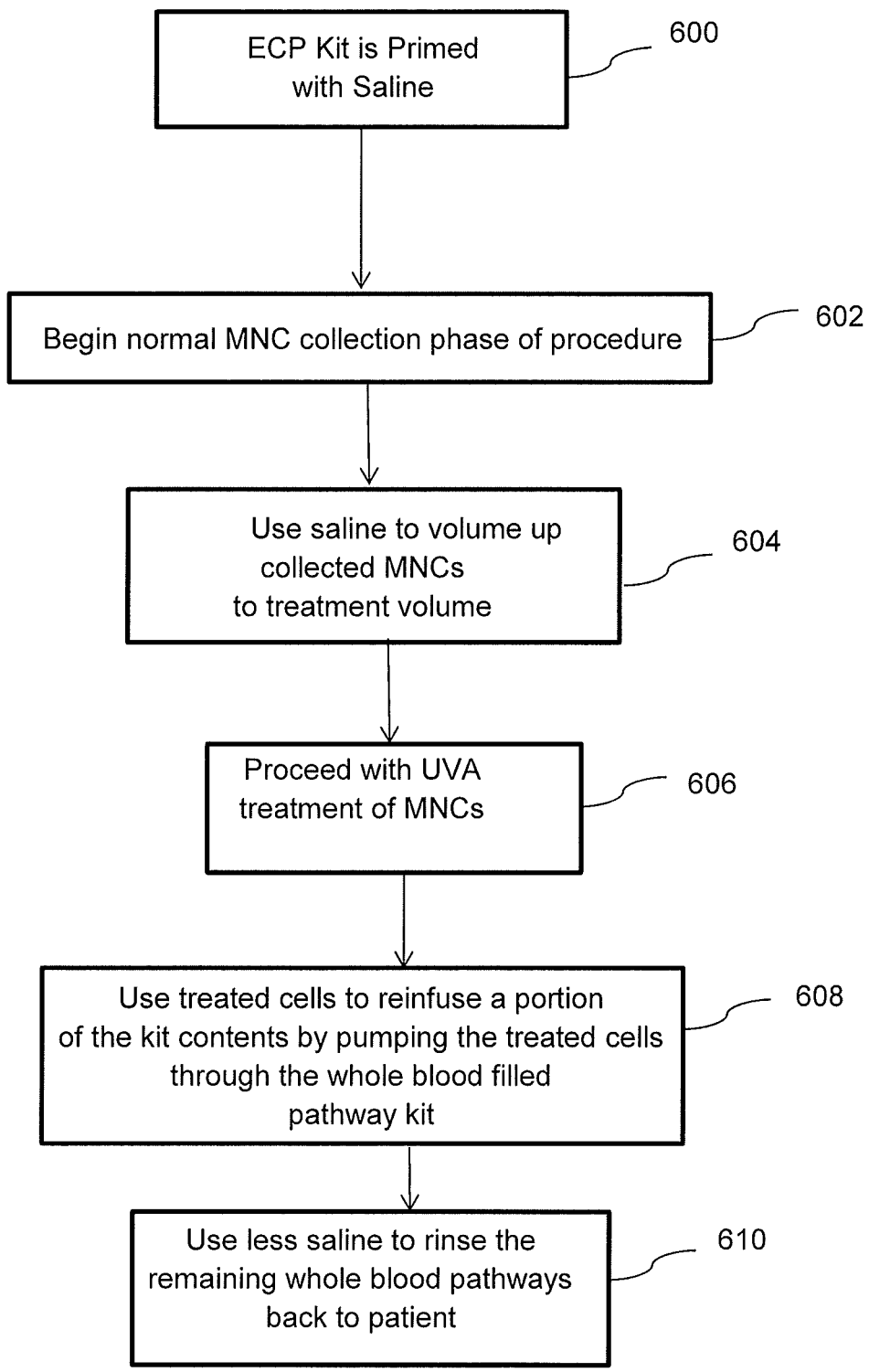
FIG. 10 is a flow chart indicating the steps of still another embodiment of the method of the present disclosure.

In accordance with another way of reducing the amount of saline that is administered to the patient, the fluid circuit may be primed with saline, as described previously (Step 600 of FIG. 10), and the normal collection of mononuclear cells is performed (Step 602). As in earlier embodiments, saline is added to increase the volume of the mononuclear cells to arrive at a treatment ready volume (step 604). The system then conducts the irradiation treatment on the mononuclear cell product (step 606). In accordance with this alternative embodiment, instead of reinfusing treated cells first and then remaining contents afterwards, i.e., in a separate step, the treated cells may be used to rinse out a portion of the disposable fluid circuit 200 (Step 608). Thereby, in accordance with this alternative method, less saline is used to rinse the remaining whole blood pathways back to the patient (Step 610).

Figure 11:
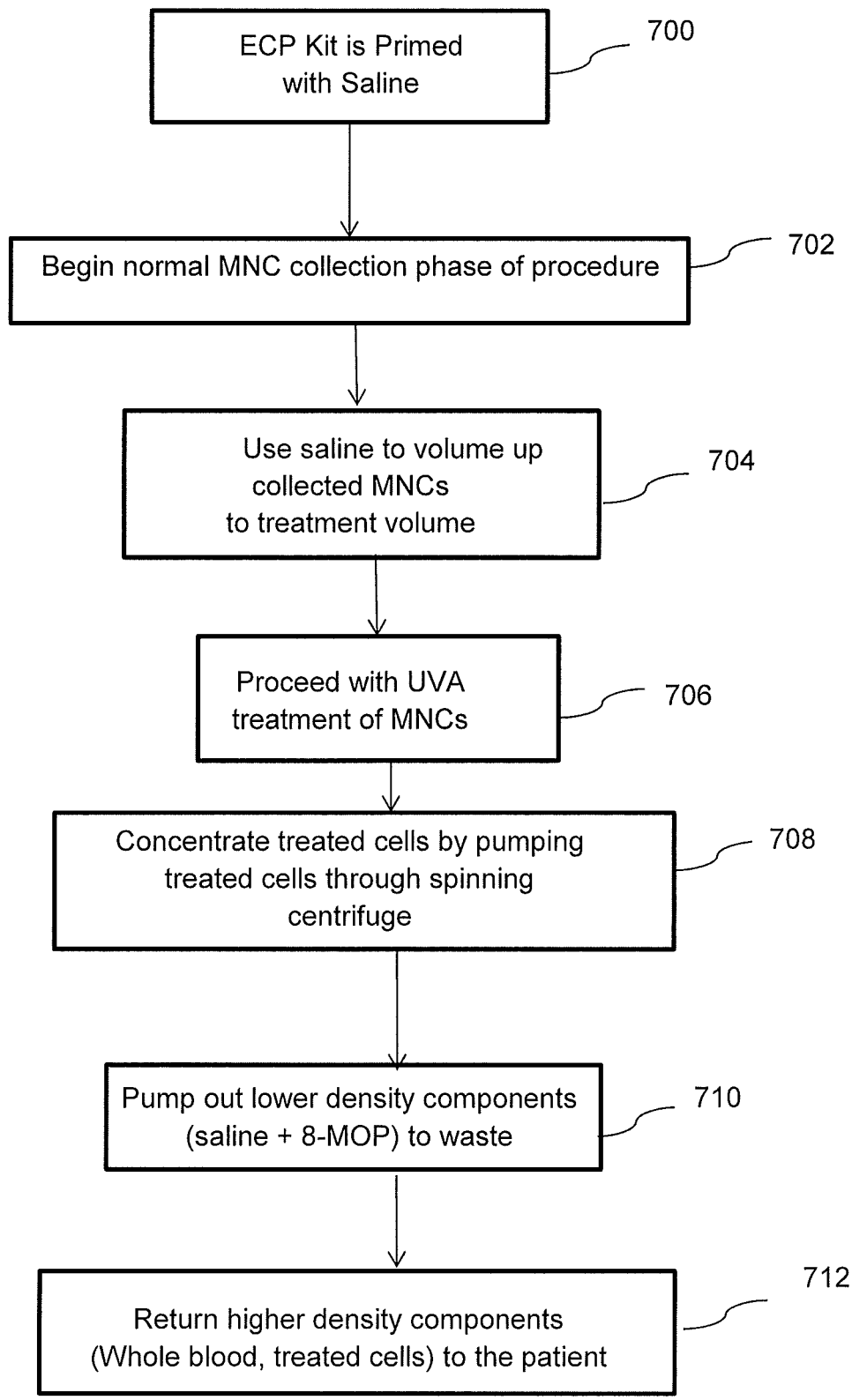
FIG. 11 is a flow chart indicating the steps of a still further embodiment of the method of the present disclosure.

In a further alternative shown in FIG. 11, the disposable fluid circuit 200 is primed with saline, as generally described above. Normal mononuclear cell collection then follows, as previously described and as shown in Step 702. Saline is used to prime circuit 200 and to adjust the volume of the collected mononuclear cells to the appropriate treatment ready volume (step 704), and the product is then subjected to the treatment step (Step 706). In accordance with this alternative embodiment, rather than simply return the treated mononuclear cell product to the patient 100, treated cells may be concentrated by conveying such treated cells to the centrifuge where they may be concentrated to a smaller volume. Lower density supernatant which may include saline and some of the photoactivation agent will be diverted to the waste container 66 (Step 710). This method of concentrating the treated mononuclear cells while diverting extra saline and additional photoactivation agent in the supernatant is described, for example, in U.S. patent application Ser. No. 14/828,226, the contents of which is hereby incorporated by reference. By returning only the higher density components such as whole bloods and treated cells to the patient, the infusion of excessive saline to the patient may be avoided (Step 712).

Other Aspects

There are additional aspects to the methods and systems described above including, without limitation, those set forth below.

Aspect 1. A method for maintaining fluid balance in a patient undergoing a therapeutic cellular treatment including: priming a fluid flow path of a disposable fluid circuit mounted on a reusable hardware unit with a predetermined volume of a priming solution; diverting at least a portion of said pre-determined volume of said priming solution from the flow path of the fluid circuit; collecting target cell population from a patient in fluid communication with the fluid circuit; combining the diverted priming solution with the target cell population to arrive at a treatment-ready product; treating the treatment-ready product to arrive at a treated cellular product; administering the treated cellular product to the patient.

Aspect 2. The method of Aspect 1 wherein the priming solution comprises saline.

Aspect 3. The method of Aspect 1 further including combining a treating agent with the target cell population.

Aspect 4. The method of any one of Aspects 1 through 3 wherein the target cell population comprises mononuclear cells.

Aspect 5. The method of any one of Aspects 1 through 4 wherein the hardware unit comprises a centrifuge and the disposable fluid circuit comprises a separation chamber mounted on the centrifuge, said method further comprising introducing whole blood from said patient into said separation chamber, spinning said centrifuge to cause said whole blood to separate into blood components and removing said priming solution from said separation chamber.

Aspect 6. The method of Aspect 5 including rotating the centrifuge to maintain an interface between the priming solution and a blood component.

Aspect 7. The method of Aspect 6 comprising detecting the location of the interface.

Aspect 8. The method of Aspect 7 further comprising pumping at least said priming fluid out of the separation chamber by action of a pump on the hardware unit.

Aspect 9. The method of Aspect 8 further including: detecting a change in the location of the interface; continuing to pump at least the priming fluid out of the separation chamber for a predetermined period of time.

Aspect 10. The method of Aspect 9 comprising combining the priming fluid pumped from said separation chamber with the collected target cell population.

Aspect 11. The method of any one of Aspects 9 through 10 comprising collecting the priming solution in a container of the fluid circuit.

Aspect 12. The method of any one of Aspects 1 through 11 further comprising concentrating the treated cell product prior to administering thes treated cell product to said patient.

Aspect 13. The method of any one of Aspects 1 through 12 comprising flowing the treated cell product through a portion of the fluid circuit prior to administering the treated cell product to the patient.

Aspect 14. A method for maintaining fluid balance in a patient undergoing a therapeutic cellular treatment including: priming a fluid flow path of a disposable fluid circuit mounted on a reusable hardware unit with a predetermined volume of a priming fluid; collecting target cell population from a patient in fluid communication the said fluid circuit; combining a solution different from said priming fluid with said target cell population to arrive at a treatment-ready product; treating the treatment-ready product to arrive at a treated cellular product; administering the priming solution to the patient; and administering the treated cellular product to the patient.

Aspect 15. The method of Aspect 16 wherein the priming fluid comprises anticoagulated whole blood.

Aspect 16. The method of any one of Aspects 14 through 15 wherein the solution different from the priming fluid comprises saline.

Aspect 17. The method of any one of Aspects 1 through 16 comprising combining a solution with the target cells to arrive at a predetermined hematocrit.

Aspect 18. The method of Aspect 17 including combining the solution with the target cell population in a volume selected to arrive at the predetermined hematocrit.

Aspect 19. The method of any one of Aspects 1 through 18 further including combining the target cell population with a predetermined volume of plasma to arrive at a treatment-ready product, the treatment ready product comprising target cell population, plasma and the priming or other solution.

Aspect 20. A system for performing a therapeutic cellular treatment including: a separation unit for effecting separation of whole blood into two or more components; a treatment unit for treating said target cell population; a disposable fluid circuit comprising a patient access device, tubing defining a flow path between the patient access device and a separation chamber, a treatment chamber and one or more containers for collecting a separated component; one or more pumps and one or more valves adapted to interact with the flow paths of the fluid circuit and effect flow of fluid through the flow paths; a detector configured to monitor the separation of whole blood into said two or more components; and a controller configured to: receive signals from said detector; and effect operation of the one more pumps to divert at least a portion of a priming solution from the flow path of said circuit to the one or more containers for collecting a separated component.

Aspect 21. The system of Aspect 20 wherein said detector is configured to detect an interface between a priming solution and a blood component.

Aspect 22. The system of Aspect 21 wherein the controller is configured to effect operation of said one or more pumps for a predetermined period of time to pump a predetermined volume of fluid within said fluid circuit between the detector and a container for collecting a separated component when the detector senses a change in said interface.

Aspect 23. The system of Aspect 22 wherein the controller is configured to effect the collection of a separated component after the predetermined volume of fluid between the detector and said container has been pumped.

Aspect 24. The system of any one of Aspects 20 through 23 wherein the separation unit comprises a centrifuge that receives a separation chamber of the fluid circuit and the treatment unit comprises an illumination device that receives said treatment chamber of the fluid circuit.

Aspect 25. The system of any one of Aspects 20 through 24 wherein the treatment unit and said separation unit are housed in separate devices.

Aspect 26. The system of any one of Aspects 20 through 25 wherein the controller is configured to effect recirculation of whole blood between a patient and a portion of the disposable fluid circuit.

Aspect 27. The system of Aspect 26 wherein the controller is configured to cause a portion of the whole blood being recirculated to be introduced into the separation chamber and divert said at least a portion of a priming solution to the one or more containers for collecting a separated component.

Aspect 28. The system of any one of Aspects 20 through 27 wherein the controller is configured to effect the delivery of a solution from the one or more containers to the treatment chamber in a volume sufficient to arrive at a predetermined hematocrit for a target cell population concentration.

Aspect 29. The system of any one of Aspects 20 through 28 wherein the controller is configured to effect the administration of a treated cell product to a patient.

Aspect 30. The system of any one of Aspects 20 through 29 wherein the priming solution is saline and said controller is configured to divert a portion of saline to the treatment chamber to arrive at a treatment-ready product.

It will be understood that the embodiments and examples described above are illustrative of some of the applications or principles of the present subject matter. Numerous modifications may be made by those skilled in the art without departing from the spirit and scope of the claimed subject matter, including those combinations of features that are individually disclosed or claimed herein. For these reasons, the scope hereof is not limited to the above description but is as set forth in the following claims, and it is understood that the claims may be directed to the features thereof, including as combinations of features that are individually disclosed or claimed herein.

The invention claimed is:

1. A system for performing a therapeutic cellular treatment comprising:
   a) a cell separation device for effecting separation of whole blood into two or more components including a target cell population;
   b) a treatment chamber for treating said target cell population;
   c) a disposable fluid circuit comprising a patient access device, tubing defining a flow path between said patient access device and a separation chamber, said treatment chamber and one or more collection containers;
   d) one or more pumps and one or more valves adapted to interact with said flow paths of said fluid circuit and effect flow of fluid through said flow paths;
   e) a detector configured to monitor the separation of whole blood into said two or more separated components; and
   f) a controller configured to:
      i. receive signals from said detector;
      ii. effect operation of said one or more pumps to introduce a priming solution into said fluid circuit;
      iii. effect the operation of said one or more pumps to introduce whole blood from a whole blood source into said fluid circuit;
      iv. effect the operation of said one or more pumps to maintain an interface between said priming solution and plasma that has been separated from said whole blood and allow said priming solution to be diverted from the flow path of said circuit to said one or more containers for collecting a separated component.

2. The system of claim 1 wherein said controller is configured to effect operation of said one or more pumps for a predetermined period of time to pump a predetermined volume of fluid within said fluid circuit between said detector and container for collecting a separated component or said treatment chamber when said detector senses a change in said interface.

3. The system of claim 2 wherein said controller is configured to commence the collection of said target cell population after said predetermined volume of fluid between said detector and said container has been pumped.

4. The system of claim 1 wherein said cell separation unit device comprises a centrifuge that receives said separation chamber of said fluid circuit and said treatment unit comprises an illumination device that receives said treatment chamber of said fluid circuit.

5. The system of claim 1 wherein said treatment chamber and said cell separation are separately housed.

6. The system of claim 1 wherein said controller is configured to effect recirculation of whole blood between a patient and a portion of said disposable fluid circuit.

7. The system of claim 6 wherein said controller is configured to cause a portion of said whole blood being recirculated to be introduced into said separation chamber and divert said at least a portion of the priming solution to said one or more containers.

8. The system of claim 1 wherein the controller is configured to effect the delivery of a solution from said one or more containers to said treatment chamber in a volume selected to arrive at a predetermined hematocrit for a target cell population concentration.

9. The system of claim 1 wherein said controller is configured to effect the administration of a treated cell product to a patient.

10. The system of claim 1 wherein the priming solution is saline and said controller is configured to divert a portion of said saline to said treatment chamber to arrive at a treatment-ready product.

11. The system of claim 1 wherein the targeted cell population comprises mononuclear cells.

12. The system of claim 1 wherein said controller is configured to effect pumping of diverted priming solution from said one of said one more containers to said treatment chamber.

13. The system claim 1 wherein said controller is configured to effect operation of said one or more pumps when said detector detects plasma during priming.

* * * * *